United States Patent [19]
Nelson et al.

[11] Patent Number: 5,456,676
[45] Date of Patent: Oct. 10, 1995

[54] ROTATABLE BUBBLE-FREE CONNECTOR

[75] Inventors: Arlin D. Nelson, Midvale; Larry B. Mitton, Bountiful; Jerry L. Trujillo, Plain City; Marshall T. Denton, Salt Lake City, all of Utah

[73] Assignee: Merit Medical Systems, Inc., South Jordan, Utah

[21] Appl. No.: 198,609

[22] Filed: Feb. 18, 1994

[51] Int. Cl.⁶ .................................................. A61M 25/00
[52] U.S. Cl. ............................................. 604/283; 604/905
[58] Field of Search ...................... 604/283, 905, 604/246, 257, 258, 274, 256, 167

[56] References Cited

U.S. PATENT DOCUMENTS

| | | | |
|---|---|---|---|
| 5,147,336 | 9/1992 | Wendell et al. | 604/283 |
| 5,284,134 | 2/1994 | Vaughn et al. | 604/283 X |
| 5,312,352 | 5/1994 | Leschinsky et al. | 604/905 X |
| 5,338,314 | 8/1994 | Ryan | 604/283 X |
| 5,364,377 | 11/1994 | O'Neil | 604/905 X |

*Primary Examiner*—John D. Yasko
*Attorney, Agent, or Firm*—Workman Nydegger Seeley

[57] ABSTRACT

A connector for connecting two catheters and permitting the catheters to rotate relatively, the connector having a collar, a hub and a rotator, the hub and the rotator having an O-Ring therebetween. The rotator overlays the hub and has an internal surface that has a shape that is contoured to the shape of the O-Ring to make a seal therebetween. The hub has a surface at an end thereof with a projection thereon that biases the O-Ring into a sealing contact with the internal contoured surface of the rotator. The collar prohibits the hub from withdrawing from its overlaid position within the rotator by overhanging a surface extending radially from the hub. The hub receives a catheter, at the end opposite its contact with the O-Ring, the catheter wedging within the hub. The rotator received a catheter by an end having a luer lock with a common longitudinal axis about which they are all preferably symmetrical. Each component, including the O-Ring is preferably concentrically aligned.

32 Claims, 3 Drawing Sheets

ROTATABLE BUBBLE-FREE CONNECTOR

BACKGROUND

1. Field of the Invention

The field of the invention is in the area of connectors between two catheters in a medical environment and is more particularly within the field of connectors that allow two connected catheters, in fluid communication with each other, to rotate relative to each other.

2. Background Art

Catheters are used by health care providers for intracorporeal insertion for the purpose of communicating fluids to and from a patient. When a first catheter is required to be in fluid communication with a second catheter, a connector must be employed therebetween. It is advantageous to provide a connector that permits the first catheter to rotate relative to the second catheter, the advantage being that the catheters are easier to manipulate and unlikely to be damaged by such manipulation.

Rotatable connectors may be used in conjunction with fluid manifolds where a rotatable connector provides a dynamic union between two catheters. Fluid manifolds serve in the role of distribution and communication of other fluids to and from a patient. Fluid manifolds with rotatable connectors may be used in procedures such as angioplastids, angiograms, and in radiology processes involving catheters or plastic tubing where there is a concern with debubbling fluids that pass through the catheters. Rotatable connectors are particularly useful in blood pressure monitoring systems that involve catheter tubing.

In medically related applications for rotatable connectors, it is particularly hazardous to permit unwanted gas bubbles from being entrained within the fluid communicated through intracorporeally inserted catheters to the site of intracorporeal insertion. For example, air bubbles entrained in a saline solution being communicated through catheters to a catheterized heart for the purpose of monitoring the subject patient's circulatory system can be lethal. Such air bubble entry can occur at a catheter connector, rotatable or otherwise, if the connector is subject to leaks and the pressure inside the connector is significantly different than the ambient pressure. Accordingly, it would be an advance in the art to avoid connector leaks.

Gas bubbles that are trapped in the rotatable connector at the time of manufacture are similarly to be avoided for like reasons. It would be an advantage to manufacture a rotatable connector that was free of bubbles trapped inside the rotatable connector.

BRIEF SUMMARY AND OBJECTS OF THE INVENTION

The present invention seeks to resolve the above and other problems which have been experienced in the art. Resolution of these problems is accomplished by the apparatus of this invention which constitutes an advancement in rotatable connectors by minimizing the entry of air into the fluid communication passageway created by the connection of two catheters with a connector.

It is a primary object of the present invention to provide a connector that permits the first catheter to rotate relative to the second catheter.

It is another important object of the present invention to provide a two catheter connector that allows one catheter to rotate relative to the other while safeguarding against air from entering at the catheter connector, the connector forming a bubble free dynamic union of the two catheters.

A further objective of the present invention is to provide a two-catheter connector that is free of trapped air bubbles within the connector at the time of manufacture, which air bubbles would otherwise gain entry to the catheters connected thereto during use of the connector.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, a rotatable catheter connector is provided having a collar, a hub and a rotator. The hub and the rotator each receive a separate catheter. The catheter received by the rotator will be preferably connected to a rotator fluid passageway within the rotator by a luer lock connector. The catheter received by the hub is advanced into a friction fit in the interior of the hub through a hub fluid passageway. Alternatively, the interior of the hub may be tapered to receive a tapered mating tube made of medical grade plastic.

The hub and the rotator having an O-Ring positioned therebetween to form an air-tight seal between the hub fluid passageway and the rotator fluid passageway. The rotator overlays the hub and has an internal contoured surface that has a shape that is contoured to the shape of the O-Ring. The hub has a surface at an end thereof with a projection thereon that biases the O-Ring into contact with the internal contoured surface of the rotator.

The air-tight seal formed by the O-Ring keeps air out of the fluid passageways in the connector by making a sealing contact with both the hub, the O-Ring, and the rotator and maintains the biasing force of the projection of the hub on the O-Ring. The air-tight seal between the hub and the rotator is maintained by the collar which prohibits the hub from withdrawing from its overlaid position within the rotator. The collar overhangs a surface extending from the hub and is attached to an outer surface on the rotator so as to permit the free rotation of the rotator about the hub.

The rotator, hub, O-Ring, and collar are all preferably symmetrical and concentrically aligned about a common longitudinal axis.

The rotator has a proximal end and a distal end with the rotator fluid passageway extending therebetween. The luer-lock connector of the rotator is at the proximal end thereof. The collar and the rotator rotate about the common longitudinal axis relative to the hub.

The hub has a proximal end and a distal end with the hub fluid passageway extending therebetween. The distal end of the hub receives an end of the catheter within the hub fluid passageway. The proximal end of the hub is received within the distal end of the rotator.

The projection of the hub biases the O-Ring in the proximal direction. The O-Ring sealingly contacts the hub at both a distally facing surface on the hub and also at an outwardly facing surface on the proximal end of the hub. The area provided within the rotator for receiving the O-Ring is designed to minimize the amount of air trapped between the hub and the rotator when the O-Ring is installed therein at the time of manufacture of the rotatable connector.

The collar preferably fastens onto the rotator by an adhesive, rather than by heating and conformingly bending the collar around the rotator, so that both production costs and energy are saved. A UV setting adhesive is preferably used to wick down into a crevice between both an outwardly facing surface on the rotator and surface of the collar.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENTS

While the following describes preferred embodiments of the present invention, the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Figure 1:
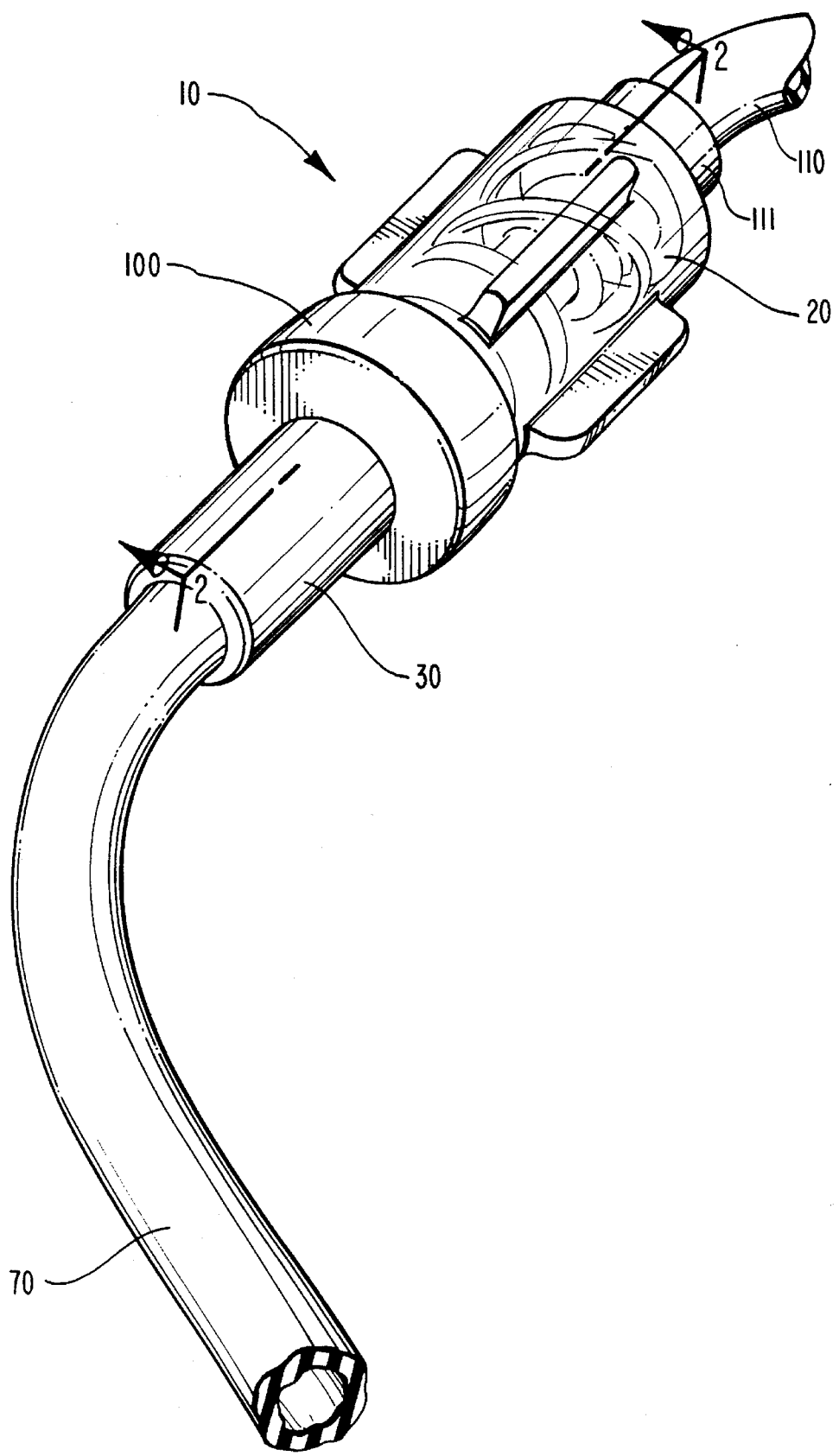
FIG. 1 is a perspective view of a bubble free rotatable connector of the present invention.

A preferred embodiment of the present invention is shown in FIG. 1 and is referred to herein as a bubble free rotatable connector 10.

FIG. 1 depicts an end of a catheter 70 advanced into a distal end of a hub 30. A rotator 20 can be connected to an end of catheter 110 at the proximal end of rotator 20. The connection of rotator 20 to catheter 110 is accomplished by a luer-lock connector at the proximal end of rotator 20. A collar 100 connects rotator 20 to hub 30 and is situated between the proximal end of rotator 20 and the distal end of hub 30.

Figure 2:
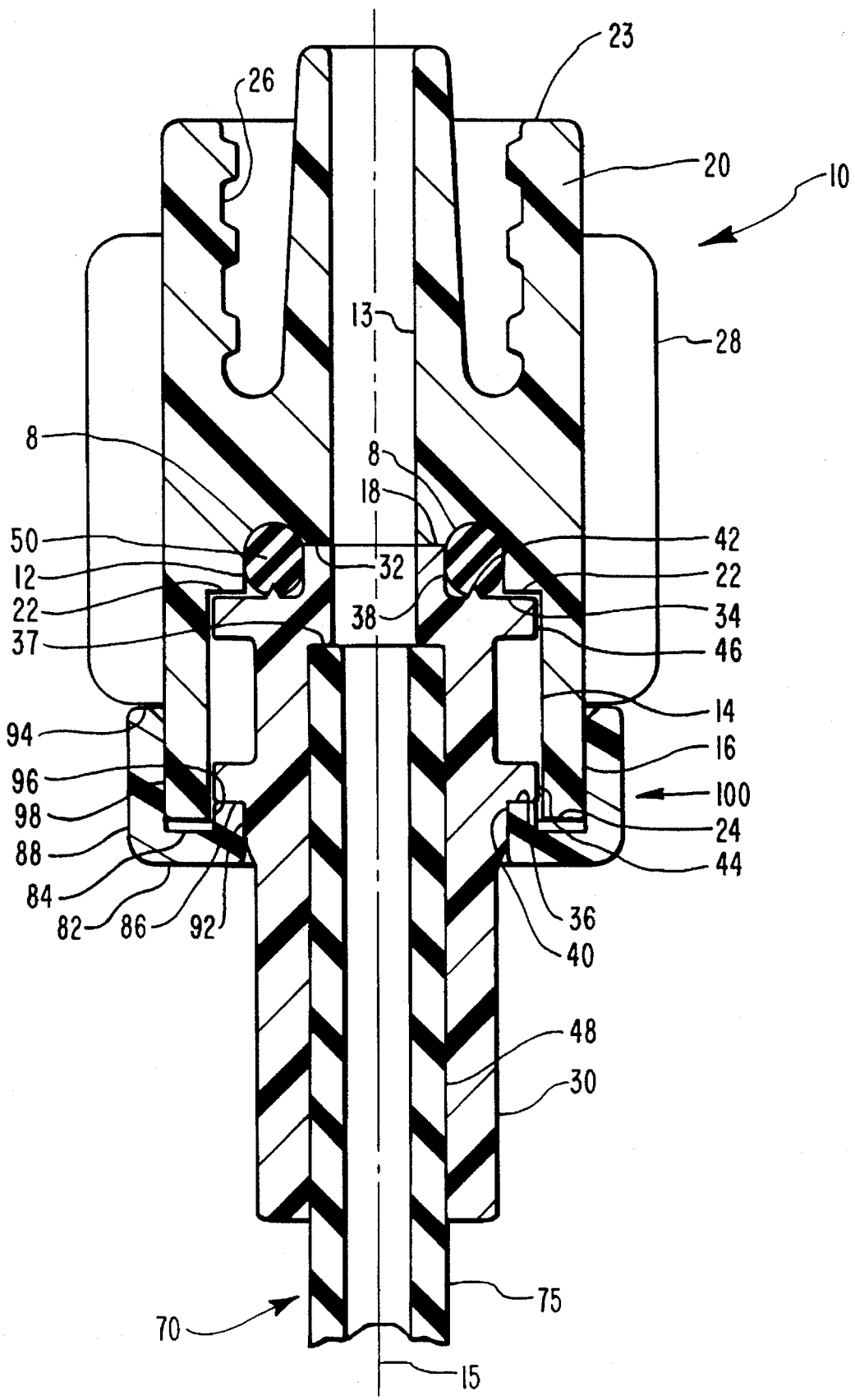
FIG. 2 is a sectional view taken along the 2—2 line of FIG. 1.
Figure 3:
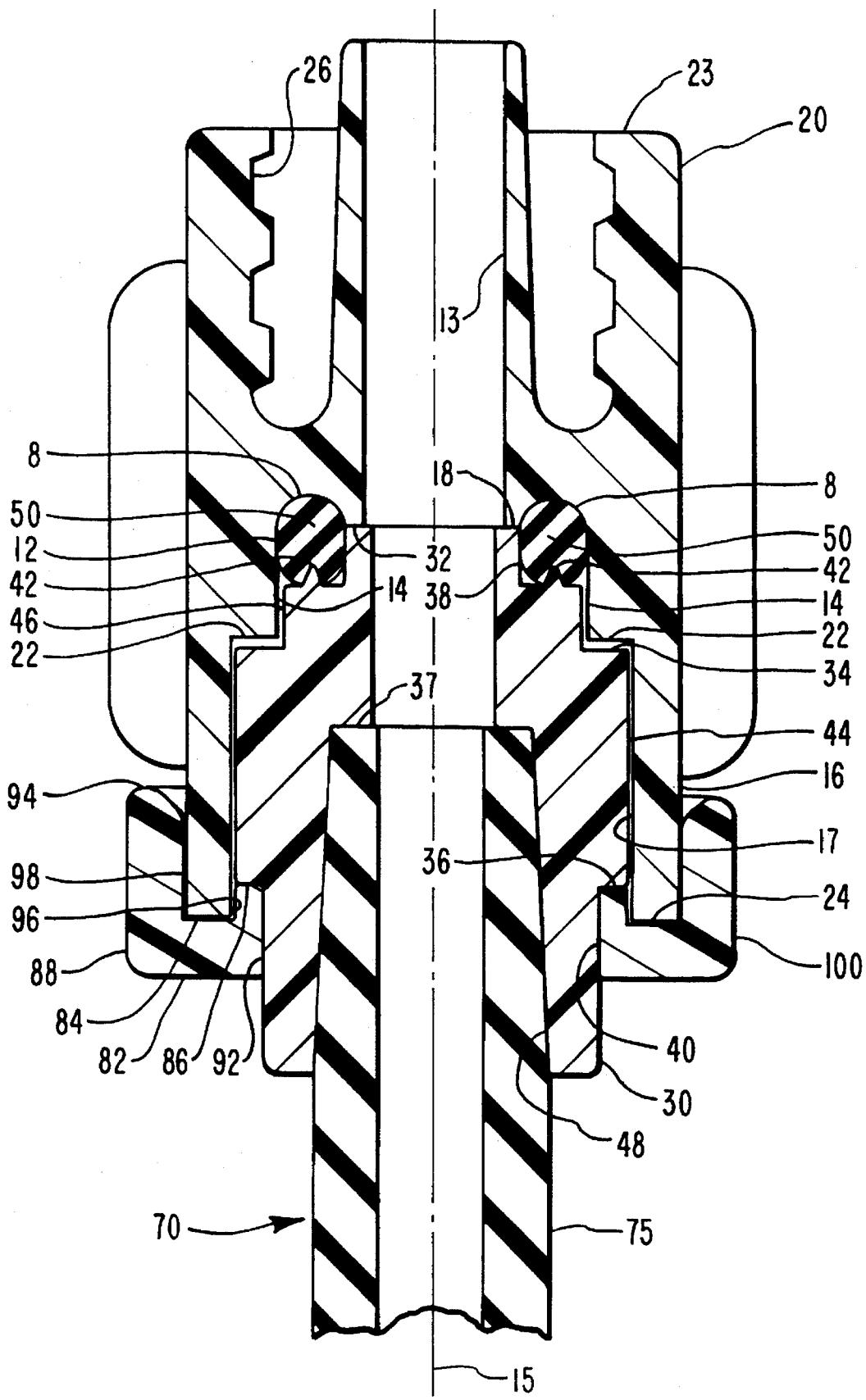
FIG. 3 is sectional view also taken along the 2—2 line of FIG. 1 showing, however, an alternative embodiment of a bubble free rotatable connector of the present invention.

Referring to FIGS. 2 and 3, the term 'proximal' or 'proximally' is intended herein to mean the direction toward the top of each of FIGS. 2 and 3, and the term 'distal' or 'distally' to mean the direction towards the bottom of each of FIGS. 2 and 3.

The embodiments shown in FIGS. 2 and 3 illustrates that rotator 20, hub 30, and collar 100 are respectively concentrically disposed and share a common central longitudinal axis 15 about which they are all symmetrical. Each of rotator 20, hub 30, and collar 100 have surfaces thereon which are either parallel to or are normal to common longitudinal axis 15.

Hub 30 has first, second, third and fourth normal surfaces 32, 34, 36, 37 that are external on hub 30 and are radially disposed perpendicular to common longitudinal axis 15. Hub 30 also has first, second, third and fourth parallel surfaces 38, 40, 44, 46 that are parallel to common longitudinal axis 15.

Rotator 20 has first, second, third and fourth normal surfaces 18, 22, 23 and 24 that are circular and normal to the common longitudinal axis. Rotator 20 also has first, second, third, and fourth parallel surfaces 12, 13, 14, and 16 that are circular and parallel to common longitudinal axis 15.

Collar 100 has first, second, third and fourth normal surfaces 82, 94, 86, and 84 that are circular and normal to common longitudinal axis 15. Collar 100 is L-shaped and has first, second, third, and fourth parallel surfaces 88, 92, 96 and 98 that are parallel to common longitudinal axis 15.

In order to keep the inventive rotatable bubble free connector air-tight, there is provided a means for providing fluid-tight fluidic communication from one catheter to the other through the hub and the rotator. By way of example and illustration of this means, a circular resilient interface part is shown in FIGS. 2 and 3 as an O-Ring 50. O-Ring 50 is internally placed within rotatable connector 10 to interface at opposing surfaces of hub 30 and rotator 20. Preferably, O-Ring 50 is not lubricated.

Further shown in FIGS. 2 and 3 is hub 30 having a distal end and a proximal end with a proximally facing surface 34 thereon. Hub 30 has a hub fluid passageway 48 between its proximal and distal ends. Both hub 30 and hub fluid passageway 48 are symmetrical about common longitudinal axis 15.

In the embodiment shown in FIG. 2, a proximal facing surface 34 is situated on hub 30. Hub 30 has a first circular ridge 32/38, also referred to herein as a diametrically reduced cylindrical extension 32/38, formed by a proximally facing circular surface 32 and an outwardly facing cylindrical surface 38, which extends normal or perpendicular to proximal facing surface 34 of hub 30. First circular ridge 32/38 extends from proximal facing surface 34 of hub 30 for a distance being called herein a first ridge height. The first ridge height preferably extends above the mid point of the thickness of O-Ring 50. Thus, first circular ridge 32/38 extends beyond and proximally of a center line that longitudinally divides O-Ring 50 into halves. The first circular ridge 32/38 is both concentric to and flush with hub fluid passageway 48, as well as symmetrical to common longitudinal axis 15. A shoulder 34/46 is formed by proximally facing surface 34 and fourth parallel surface 46 of hub 30.

In both the embodiments of FIGS. 2 and 3, hub 30 also has a second circular ridge 36/44 which is formed by a distally facing surface 36, and by an outwardly facing surface 44 which is parallel to common longitudinal axis 15 and is situated between the proximal and distal ends of hub 30 and extends normal to common longitudinal axis 15. Hub fluid passageway 48 is fashioned to receive catheter 70 therein. The lumen through catheter 70 is in fluid communication with a rotator fluid passageway 13 that passes through rotator 20.

FIGS. 2 and 3 show O-Ring 50 as concentric with hub fluid passageway 48 and symmetrical about common longitudinal axis 15. O-Ring 50 is situated so that it has one half proximal to and the other half distal to a plane normal to common longitudinal axis 15 that passes through the geometric center of O-Ring 50. The outwardly facing surface 38 of first circular ridge 32/38 of hub 30 makes a sealing contact with O-Ring 50. The distal half of O-Ring 50 is below the most proximal end of hub 30, while the proximal half of O-Ring 50 extends proximally of the most proximal end of hub 30.

A circular projection 42 is situated on the proximal end of hub 30 and makes a contact with the distal half of O-Ring 50. Projection 42 enhances the seal between hub 30 and rotator 20 by biasing O-Ring 50 in the proximal direction into contact with a circular recessed channel 8, alternatively referred to herein as a distally facing arcuate groove 8 of rotator 20, described below.

The volume provided between rotator 20 and hub 30 for retaining O-Ring 50 is quite small so as to minimize the possibility of trapped air bubbles therein at the time of manufacture.

As shown in FIGS. 2 and 3, rotator 20 has a cylindrical cavity 14, 14, 22, 12, 8, 18, a proximal end and has a distal end with a distally facing surface 24 thereon. Rotator fluid passageway 13 is symmetrical about common longitudinal axis 15 and lies between the distal and proximal end of rotator 20.

The rotator of the inventive rotatable bubble free catheter connector also features a threadable connecting means for connecting rotator to a catheter. An example of such a connecting means is a luer lock connector with internal threading 26 at the proximal end of rotator 20 for receiving threadable connectors. Preferably, catheter 110 will be connected via internal threading 26.

An internal distally facing circular surface 18, which is concentric with rotator fluid passageway 13, contacts proximally facing cylindrical surface 32 of first circular ridge 32/38 of hub 30.

Distally facing arcuate groove 8 is juxtaposed to distally facing first circular surface 32 of hub 30. Groove 8 is juxtaposed to a first parallel surface 12 which is cylindrical, internally facing, and both parallel to and symmetrical about longitudinal common axis 15. Groove 8 makes a conforming and sealing contact with the proximal portion of O-Ring 50.

Rotator 20 has a first circular ridge 16/24, formed both by a distally facing surface 24 on the distal end of the rotator 20 and by an outwardly facing surface 16. First circular ridge 16/24 is concentric with the rotator fluid passageway 13 and is symmetrical about common longitudinal axis 15. First circular ridge 16/24 of rotator 20 both overlays and makes contact with outwardly facing surface 44 of second circular ridge 36/44 of hub 30.

Collar 100 makes contact with distally facing surface 36 of second circular ridge 36/44 of hub 30. Collar 100 is rigidly affixed to first circular ridge 16/24 of rotator 20. By so affixing collar 100, rotator 20 can rotate relative to hub 30 about common longitudinal axis 15, while hub 30 is restricted from movement along common longitudinal axis 15 relative to rotator 20.

Collar 100 can be attached or fixed to first circular ridge 16/24 of rotator 20 by an adhesive such as a UV setting adhesive which, when applied to surface 16 or rotator 20 preferably will be permitted to wick down between surface 16 of rotator 20 and surface 98 of collar 100 before being exposed to UV light so as to cause adherence between these two surfaces. These two surfaces can also be affixed by ultrasonic welding. Hub 30 and rotator 20 are preferably constructed of medical grade plastic.

In a first preferred embodiment, as shown in FIG. 2, first parallel surface 12 of rotator 20 extends from arcuate groove 8 of rotator 20 up to proximally facing surface 34, and ends at a distally facing second circular platform 22 of rotator 20. Both first parallel surface 12 of rotator 20 and second circular surface 22 of rotator 20 are juxtaposed to, but do not contact proximally facing surface 34 on the proximal end of hub 30. FIG. 2 also shows that the following surfaces are not in contact with each other so as to reduce friction during rotation of rotator 20 relative to hub 30 about common longitudinal axis 15: surfaces 44 and 14, surfaces 40 and 92, and surfaces 24 and 84.

The outer diameter of proximally facing surface 34 is larger than that of O-ring 50.

In a second preferred embodiment, as shown in FIG. 3, first parallel surface 12 of rotator 20 extends from arcuate groove 8 of rotator 20 past proximal facing surface 34 on the proximal end surface of hub 30, to be parallel to an outwardly facing cylindrical surface 46 on hub 30, and ends at a distally facing second circular platform 22 of rotator 20. The seal by O-Ring 50 between both hub 30 and rotator 20 is a piston-type seal. FIG. 3 also shows that the following surfaces are not in contact with each other so as to reduce friction during rotation of rotator 20 relative to hub 30 about common longitudinal axis 15, surfaces 44 and 14, surface 46 and 12, surfaces 40 and 92, and surfaces 24 and 84.

The outer diameter of proximally facing surface 34 is approximately equal to that of O-ring 50.

In both FIGS. 2 and 3, the seal to present entry of air in fluid passageways through rotator 20 and hub 30 is made by contacts between surfaces 18 and 32, and between O-Ring 50 with surfaces 8 and 38. To aid in the absence of trapped air, zero tolerance is preferable between surfaces 18 and 32.

In summary, the present invention provides a connector that connects two catheters that are in fluid communication with each other, allowing one catheter to rotate relative to the other, while providing a seal at the connector that is resistant to the passage of air into a lumen formed at the connector between the two catheters.

The present invention may be embodied in other specific forms with departing from its spirit or essential characteristics. The described embodiments are to be considered in all respects only as illustrative and not restrictive. The scope of the invention is, therefore, indicated by the appended claims rather than by the foregoing description. All changes which come with the meaning and range of equivalency of the claims are to be embraced within their scope.

What is claimed and desired to be secured by United States Patent is:

1. A catheter connector apparatus for rotatably connecting a first catheter to a second catheter so as to provide a fluid-tight fluidic communication therebetween while permitting at least one of said first and second catheters to be rotated relative to the other of said first and second catheters said catheter connector apparatus, in combination with said first and said second catheters comprising:

a rotator comprising one end having a cylindrical cavity, said cylindrical cavity having therein a circular recessed channel, and further comprising another end having a means for connection to said first catheter, said cylindrical cavity having a bore therethrough in fluid communication with said first catheter;

a hub for providing a first cylindrical bearing surface of essentially uniform diameter, said rotator being rotatably mounted on said first cylindrical bearing surface of said hub, said first cylindrical bearing surface of said hub fitting within said cylindrical cavity of said rotator in mating relationship therewith, said hub having an end with a means for connection to said second catheter, said hub further comprising a shoulder having a bore therethrough which is in fluid communication with said second catheter, said cylindrical cavity of said rotator being dimensioned to receive said shoulder of said hub in a fluid-tight fit therein; and means for providing fluid-tight fluidic seal from one of said first and second catheters to the other of said first and second catheters through said rotator and said hub, and comprising:

a circular resilient interface means, having a conforming circumferential external surface thereon to said circular recessed channel, for providing a resilient interface between said rotator and said hub, and being positioned both between said rotator and said hub, and within said circular channel so as to be received therein in a mating relationship and so as to provide a fluid-tight seal between said rotator and said hub.

2. A catheter connector apparatus as defined in claim 1, wherein said first cylindrical bearing surface of said hub has a circular projection extending therefrom and into said circular resilient interface means so as to bias said circular resilient interface means into said circular recessed channel, and so as to make a sealing contact between said circular resilient interface means and said circular channel.

3. A catheter connector apparatus as defined in claim 1, wherein said circular resilient interface means comprises an O-Ring and said circular recessed channel of said cylindrical cavity of said rotator is an arcuate circular groove of essentially semi-circular cross section making a conforming and sealing fit with said O-Ring.

4. A catheter connector apparatus as defined in claim 2, wherein said circular resilient interface means comprises an O-Ring, and wherein said circular recessed channel of said cylindrical cavity of said rotator is an arcuate circular groove of essentially semi-circular cross section making a conforming and sealing fit with said O-Ring.

5. A catheter connector apparatus as defined in claim 3, wherein said shoulder of said hub comprises a diametrally reduced cylindrical extension, said circular resilient interface means being positioned over said reduced cylindrical extension of said shoulder of said hub.

6. A catheter connector apparatus as defined in claim 1, wherein said hub further comprises a second cylindrical bearing surface on an outer surface thereof; and said catheter connector apparatus further comprises a collar comprising a first cylindrical bearing surface rotatably mounted on said second cylindrical bearing surface of said hub;

said collar being rigidly attached to said rotator, whereby said collar is immobile relative to said rotator and said hub is rotatable relative to said collar.

7. A catheter connector apparatus as defined in claim 6, wherein said one end of said rotator has thereon a first circular platform, and wherein said collar further comprises a first circular platform parallel to said first circular platform of said rotator, and wherein said collar is rigidly attached by a third surface of said collar, distinct from said first circular platform of said collar, to said rotator.

8. A catheter connector apparatus as defined in claim 1, wherein said hub further comprises a circular platform distal of said first cylindrical bearing surface of said hub, and said rotator further comprises a corresponding circular platform distal of said first cylindrical bearing surface of said hub parallel to said circular platform of said hub.

9. A catheter connector apparatus as defined in claim 1, wherein said hub further comprises a third cylindrical bearing surface at an end opposite said means for connection to said second catheter, and said cylindrical cavity of said rotator further comprises a corresponding first cylindrical bearing surface which is rotatably mounted on said third cylindrical bearing surface of said hub.

10. A catheter connector apparatus as defined in claim 4, wherein said hub further comprises a third cylindrical bearing surface at an end opposite said means for connection to said second catheter, and said cylindrical cavity of said rotator further comprises a corresponding first cylindrical bearing surface which is rotatably mounted on said third cylindrical bearing surface of said hub.

11. A catheter connector apparatus for rotatably connecting a first catheter to a second catheter so as to provide a fluid-tight fluidic communication therebetween while permitting at least one of said first and second catheters to be rotated relative to the other of said first and second catheters, said catheter connector apparatus, in combination with said first and said second catheters, comprising:

a rotator comprising one end having a cylindrical cavity and further comprising another end having a means for connection to said first catheter, said cylindrical cavity having a bore therethrough in fluid communication with said first catheter;

a hub for providing a first cylindrical bearing surface of essentially uniform diameter, said rotator being rotatably mounted on said first cylindrical bearing surface of said hub, said first cylindrical bearing surface of said hub fitting within said cylindrical cavity of said rotator in mating relationship therewith, said hub having an end with a means for connection to said second catheter, said hub further comprising a shoulder having a bore therethrough which is in fluid communication with said second catheter;

said cylindrical cavity of said rotator being dimensioned to receive said shoulder of said hub in a fluid-tight fit therein;

said shoulder of said hub comprising a diametrally reduced cylindrical extension;

said catheter connector apparatus further comprising a circular resilient interface means for providing a resilient interface between said rotator and said hub and being positioned over said reduced cylindrical extension of said shoulder of said hub, said cylindrical cavity of said rotator having a circular recessed channel for receiving therein and overlaying said circular resilient interface means in a mating relationship so as to provide a fluid-tight seal between said rotator and said hub;

said hub further comprising a second cylindrical bearing surface on the outer surface thereof, said catheter connector apparatus further comprising a collar comprising a first cylindrical bearing surface rotatably mounted on said second cylindrical bearing surface of said hub, and said collar being rigidly attached to said rotator, whereby said collar is immobile relative to said rotator and said hub is rotatable relative to said collar.

12. A catheter connector apparatus as defined in claim 11, wherein said one end of said rotator has thereon a first circular platform, and wherein said collar further comprises a first circular platform parallel to said first circular platform of said rotator, and wherein said collar is rigidly attached by a third surface of said collar, distinct from said first circular platform of said collar, to said rotator.

13. A catheter connector apparatus as defined in claim 11, wherein said hub further comprises a circular platform, and said rotator further comprises a corresponding circular platform parallel to said circular platform of said hub.

14. A catheter connector apparatus as defined in claim 11, wherein said hub further comprises a third cylindrical bearing surface at an end opposite said means for connection to said second catheter, and said cylindrical cavity of said rotator further comprising a corresponding first cylindrical bearing surface which is rotatably mounted on said third cylindrical bearing surface of said hub.

15. A catheter connector apparatus as defined in claim 11, wherein said first cylindrical bearing surface of said hub has a circular projection extending therefrom into said circular resilient interface means so as to bias said circular resilient interface means into said circular recessed channel, and so as to make a sealing contact between said circular resilient interface means and said circular recessed channel.

16. A catheter connector apparatus as defined in claim 11, wherein said circular resilient interface means comprises an O-Ring and said circular recessed channel of said cylindrical cavity of said rotator is an arcuate circular groove of essentially semi-circular cross section making a conforming and sealing fit with said O-Ring.

17. A catheter connector apparatus as defined in claim 15, wherein said circular resilient interface means comprises an O-Ring and said circular recessed channel of said cylindrical cavity of said rotator is an arcuate circular groove of essentially semi-circular cross section making a conforming and sealing fit with said O-Ring.

18. A catheter connector apparatus for rotatably connecting a first catheter to a second catheter so as to provide a fluid-tight fluidic communication therebetween while permitting at least one of said first and second catheters to be rotated relative to the other of said first and second catheters, said catheter connector apparatus, in combination with said first and said second catheters, comprising:

a rotator comprising one end having a cylindrical cavity and further comprising another end having a means for connection to said first catheter, said cylindrical cavity having a bore therethrough in fluid communication with said first catheter;

a hub for providing a first cylindrical bearing surface of essentially uniform diameter, said rotator being rotatably mounted on said first cylindrical bearing surface of said hub, said first cylindrical bearing surface of said hub fitting within said cylindrical cavity of said rotator in mating relationship therewith, said hub having an end with a means for connection to said second catheter, said hub further comprising a shoulder having a bore therethrough which is in fluid communication with said second catheter;

said cylindrical cavity of said rotator being dimensioned to receive in a fluid-tight fit therein said shoulder of said hub;

said shoulder of said hub comprising a diametrally reduced cylindrical extension;

said catheter connector apparatus further comprising a circular resilient interface means for providing a resilient interface between said rotator and said hub and being positioned over said reduced cylindrical extension of said shoulder of said hub, said cylindrical cavity of said rotator having a circular recessed channel for receiving therein said circular resilient interface means in a mating relationship so as to provide a fluid-tight seal between said rotator and said hub;

said first cylindrical bearing surface of said hub having a circular projection extending therefrom and into said circular resilient interface means so as to bias said circular resilient interface means into said circular recessed channel and to make a sealing contact between said circular resilient interface means and said circular recessed channel;

said hub further comprising a second cylindrical bearing surface on an outer surface thereof, said catheter connector apparatus further comprising a collar comprising a first cylindrical bearing surface rotatably mounted on said second cylindrical bearing surface of said hub, and said collar being rigidly attached to said rotator, whereby said collar is immobile relative to said rotator and said hub is rotatable relative to said collar.

19. A catheter connector apparatus as defined in claim 18, wherein said circular resilient interface means comprises an O-Ring and said circular recessed channel of said cylindrical cavity of said rotator is an arcuate circular groove of essentially semi-circular cross section making a conforming and sealing fit with said O-Ring.

20. A catheter connector apparatus as defined in claim 18, wherein said one end of said rotator has thereon a first circular platform, and wherein said collar further comprises a first circular platform parallel to said first circular platform of said rotator, and wherein said collar is rigidly attached by a third surface of said collar, distinct from said first circular platform of said collar, to said rotator.

21. A catheter connector apparatus as defined in claim 18, wherein said hub further comprises a circular platform distal of said first cylindrical bearing surface of said hub, and said rotator further comprises a corresponding circular platform distal of said first cylindrical bearing surface of said hub parallel to said circular platform of said hub.

22. A catheter connector apparatus as defined in claim 18, wherein said hub further comprises a third cylindrical bearing surface at an end opposite said means for connection to said second catheter, and said cylindrical cavity of said rotator further comprising a corresponding first cylindrical bearing surface which is rotatably mounted on said third cylindrical bearing surface of said hub.

23. A bubble free rotatable connector having a proximal end and a distal end and a common longitudinal axis extending therebetween, comprising:

a hub having a proximal end and a distal end and a cylindrical hub passageway therebetween, said proximal end of said hub having a proximally facing surface thereon, both said hub and said hub cylindrical passageway being symmetrical about said common longitudinal axis, said proximal end of said hub having a first circular ridge extending both normal thereto and proximal therefrom for a distance of a first ridge height and being both concentric and flush with said hub fluid passageway and being symmetrical to said common longitudinal axis, the first circular ridge having a proximally facing circular surface and an outwardly facing cylindrical surface, said hub further comprising a second circular ridge between said proximal and distal ends of said hub which extends normal to said common longitudinal axis and has a distally facing surface and an outwardly facing surface which is parallel to said common longitudinal axis;

an O-Ring concentric with the hub fluid passageway and both symmetrical about and normal to said common longitudinal axis, and having a half of said O-Ring proximal to and a half of said O-Ring distal to a plane normal to said common longitudinal axis passing through the geometric center of said O-Ring, the distal half of the O-Ring making contact with both the proximally facing surface on the proximal end of the hub and the outwardly facing surface of the first circular ridge of said hub;

a rotator having a distal end with a distally facing surface thereon and a proximal end, and a cylindrical rotator fluid passageway therebetween, both said rotator and said rotator fluid passageway being symmetrical about said common longitudinal axis, said rotator comprising:

threadable connecting means at the proximal end of said rotator for receiving threadable connectors, a first internal distally facing circular surface that is concentric with said rotator fluid passageway and that contacts said proximally facing circular surface of said first circular ridge of said hub, an internal substantially distally facing arcuate groove that is juxtaposed to said distally facing first circular surface of said rotator, and that is juxtaposed to a first parallel surface which is internally facing, cylindrical, and both parallel to and symmetrical about said common longitudinal axis, said arcuate groove making a conforming and sealing contact with the proximal half of the O-Ring, a first circular ridge that is concentric with said rotator fluid passageway and symmetrical about said common longitudinal axis and that extends to the distally facing surface on said distal end of said rotator, said first circular ridge of said rotator both overlaying and making contact with said outwardly facing surface of second circular ridge of said hub; and a collar making contact with the distally facing surface of the second circular ridge of said hub and being rigidly affixed to the first circular ridge of said rotator, whereby said rotator rotates relative to said hub about said common longitudinal axis and is restricted from movement along said common longitudinal axis relative to said hub.

24. The bubble free rotatable connector as defined in claim 23, further comprising a circular projection on the proximal end of said hub biasing said O-Ring proximally into contact with said distally facing arcuate groove of said rotator.

25. The bubble free rotatable connector as defined in claim 23, wherein said first ridge height extends above the geometric center of the O-Ring.

26. The bubble free rotatable connector as defined in claim 23, wherein said first parallel surface of the rotator extends from said arcuate groove of said rotator to a distally facing second circular surface of said rotator proximal of said proximally facing surface of the proximal end of said hub.

27. The bubble free rotatable connector as defined in claim 25, wherein said first parallel surface of the rotator extends from said arcuate groove of said rotator to a distally facing second circular surface of said rotator proximal of said proximally facing surface on the proximal end of said hub.

28. The bubble free rotatable connector as defined in claim 23, wherein said first parallel surface of the rotator extends from said arcuate groove of said rotator past and distal of said proximally facing surface on the proximal end of said hub to parallel an outwardly facing cylindrical surface of said hub.

29. The bubble free rotatable connector as defined in claim 25, wherein said first parallel surface of the rotator extends from said arcuate groove of said rotator past and distal of said proximally facing surface on the proximal end of said hub to parallel an outwardly facing cylindrical surface of said hub.

30. A catheter connector apparatus as defined in claim 1, wherein said circular resilient interface means has an outer diameter, and said first cylindrical bearing surface of said hub has an outer diameter, and wherein the outer diameter of the circular resilient interface means is substantially equal to the outer diameter of the first cylindrical bearing surface of said hub.

31. A catheter connector apparatus as defined in claim 11, wherein said circular resilient interface means has an outer diameter, and said first cylindrical bearing surface of said hub has an outer diameter, and wherein the outer diameter of the circular cylindrical interface means is substantially equal to the outer diameter of the first cylindrical bearing surface of said hub.

32. A catheter connector apparatus as defined in claim 18, wherein said circular resilient interface means has an outer diameter, and said first cylindrical bearing surface of said hub has an outer diameter, and wherein the outer diameter of the circular resilient interface means is substantially equal to the outer diameter of the first cylindrical bearing surface of said hub.

\* \* \* \* \*

UNITED STATES PATENT AND TRADEMARK OFFICE
CERTIFICATE OF CORRECTION

PATENT NO. : 5,456,676

DATED : October 10, 1995

INVENTOR(S) : ARLIN D. NELSON et al.

It is certified that error appears in the above-indentified patent and that said Letters Patent is hereby corrected as shown below:

Column 5, line 12, delete second occurrence of "14,"

Column 5, line 19, change "connecting rotator to a catheter." to --connecting rotator 20 to catheter 110.--

Column 6, lines 4-5, "The outer diameter ... O-ring 50" should be the last sentence of the paragraph ending at column 6, line 3

Column 6, lines 18-19, "The outer diameter ... O-ring 50" should be the last sentence of the paragraph ending at column 16, line 16

Column 9, line 4, after "circular" insert --platform distal of said first cylindrical bearing surface of said hub,--

Column 9, line 4, delete "platform,"

Column 9, lines 5-6, after "platform" insert --distal of said first cylindrical bearing surface of said hub,--

Signed and Sealed this

First Day of April, 1997

BRUCE LEHMAN

*Attest:*

*Attesting Officer*   Commissioner of Patents and Trademarks